(12) United States Patent
Townsend (10) Patent No.: US 9,127,271 B2
(45) Date of Patent: Sep. 8, 2015

(54) MULTI-TARGETED PRIMING FOR GENOME-WIDE GENE EXPRESSION ASSAYS

(76) Inventor: Jeffrey P. Townsend, Woodbridge, CT (US)

( * ) Notice: Subject to any disclaimer, the term of this patent is extended or adjusted under 35 U.S.C. 154(b) by 69 days.

(21) Appl. No.: 13/695,845

(22) PCT Filed: May 2, 2011

(86) PCT No.: PCT/US2011/034762
§ 371 (c)(1),
(2), (4) Date: Jan. 11, 2013

(87) PCT Pub. No.: WO2011/139955
PCT Pub. Date: Nov. 10, 2011

(65) Prior Publication Data
US 2013/0130940 A1     May 23, 2013

Related U.S. Application Data

(60) Provisional application No. 61/343,728, filed on May 3, 2010.

(51) Int. Cl.
*C12N 15/10*    (2006.01)
*C12Q 1/68*     (2006.01)

(52) U.S. Cl.
CPC ............ *C12N 15/1096* (2013.01); *C12Q 1/686* (2013.01); *C12Q 1/689* (2013.01); *C12Q 1/6895* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2003/0044791 A1*  3/2003  Flemington ...................... 435/6
2003/0073239 A1*  4/2003  Karlovsky et al. ............ 435/468
2003/0186288 A1* 10/2003  Spivack et al. .................... 435/6
2006/0008807 A1*  1/2006  O'Hara et al. ..................... 435/6

FOREIGN PATENT DOCUMENTS

WO     9955913 A2    11/1999

OTHER PUBLICATIONS

Sybesma et al. Biotechniques. Sep. 2001;31(3): pp. 466, 468, 470, 472.*
Notification of the International Search Report and Written Opinion for PCT/US2011/034762 mailed Oct. 28, 2011.
Gonzalez et al., "Counterselection of prokaryotic ribosomal RNA during reverse transcription using non-random hexameric oligonucleotides". Journal of Microbiological Methods, Elsevier, Amsterdam, NL, vol. 71, No. 3, Nov. 27, 2007, pp. 288-291, XP022363796.
Armour, Christopher D., et al., "Digital transcriptome profiling using selective hexamer priming for cDNA synthesis". Nature Methods, Nature Publishing Group, GB. vol. 6, No. 9. Sep. 1, 2009, pp. 647-649, XP009125354.
Lopez-Nieto C E, et al. "Selective amplification of protein-coding regions of large sets of genes using statistically designed primer sets". Nature Biotechnology, Jul. 1996. pp. 857-861, XP002090066.
European Communication for corresponding EP Application No. 11778094.0-140312566982 PCT/US2011034762 dated Sep. 18, 2013.

* cited by examiner

Primary Examiner — Christopher M Babic
Assistant Examiner — Sahana Kaup
(74) Attorney, Agent, or Firm — MKG LLC (57) ABSTRACT

The present invention is a method of generating a library of expressed cDNA sequences using multi-targeted primers that are complementary to degenerate motifs present in a large proportion of corresponding mRNA sequences. Multi-targeting priming (MTP) for genome-wide gene expression assays provides selective targeting of multiple sequences and counter-selection against undesirable sequences. Priming with MTPs in addition to oligo-dT can result in higher sensitivity, a greater number of genes whose expression is well measured, a greater number of genes whose differences in gene expression are detected to be statistically, and a greater power to detect meager differences in expression.

15 Claims, 5 Drawing Sheets

MULTI-TARGETED PRIMING FOR GENOME-WIDE GENE EXPRESSION ASSAYS

BACKGROUND OF THE INVENTION

1. Field of the Invention

The present invention is directed to methods of assessment of gene expression, and more particularly to methods of assessment of gene expression that utilize multi-targeted priming for genome-wide gene expression assays.

2. Description of the Related Art

Gene expression levels have been quantified by numerous procedures, including reverse transcription (RT)-PCR (Bustin S A, *J Mol Endocrinol* 2000, 25(2):169-193), sequencing of expressed sequence tags (ESTs) (Adams M D, Kelley J M, Gocayne J D, Dubnick M, Polymeropoulos M H, Xiao H, Merril C R, Wu A, Olde B, Moreno R F, *Science* 1991, 252(5013):1651-1656), serial analysis of gene expression (SAGE) (Velculescu V E, Zhang L, Vogelstein B, Kinzler K W, *Science* 1995, 270(5235):4840, microarray hybridization (DeRisi J L, Iyer V R, Brown P O, *Science* 1997, 278(5338): 680), and massively parallel signature sequencing (Nagalakshmi U, Wang Z, Waern K, Shou C, Raha D, Gerstein M, Snyder M, *Science* 2008, 320(5881):1344). Rapid development of platforms has improved throughput, but also generated strong demand for enhanced sensitivity and measurement accuracy. For nearly all expression assays, reverse transcription from messenger RNA (mRNA) to complementary DNA (cDNA) is a key step of the process that contributes less experimental variance than biological growth and harvest, but greater experimental variance than hybridization (Yang Y H, Speed T, *Nat Rev Genet* 2002, 3(8):579-588 and Wernisch L, Kendall S L, Soneji S, Wietzorrek A, Parish T, Hinds J, Butcher P D, Stoker N G, *Bioinformatics* 2003, 19(1):53-61). Throughput of the reaction may be biased by secondary and tertiary structures of mRNA, affinities specific to the reverse transcriptase, inhibitors present in the sample, priming strategy, and variation in priming efficiency (Stahlberg A, Hakansson J, Xian X J, Semb H, Kubista M, *Clinical Chemistry* 2004, 50(3):509-515). The most common priming strategies utilize oligo-dT primers, random primers, or gene-specific primers. When oligo-dT primers are used for reverse transcription, RNA secondary structure and variation in poly (A) tail length may result in gene amplification 3' bias. Random primers, often used in prokaryotic systems, fail to discriminate between mRNA and the preponderance of RNA in the form of ribosomal (rRNA) or transfer RNA (tRNA). Random hexamers, the most commonly employed, amplify only fraction of the transcriptome, comparing with random pentadecamers (Stangegaard M, Dufva I H, Dufva M, *BioTechniques* 2006, 40(5):649-657). However, random oligonucleotides of any size also prime abundant rRNAs and tRNAs that can lead to high background and misleading signal.

Ribosomal RNA (rRNA) sequences in many prokaryotes are GC rich relative to the genome at large and are highly conserved. These properties have been used to design non-random hexamers (HD/DHTTTT) to prime reverse transcription reactions (Gonzalez J M, Robb F T, *J Microbiol Methods* 2007, 71(3):288-291). The result was a counter-selective synthesis of cDNA corresponding to mRNA from prokaryotic total RNA extractions. In contrast, application of gene-specific primers on a genomic scale requires synthesis of multiple primers. An algorithm to predict the minimal number of non-degenerate genome-directed primers that specifically anneal to all genes in a given genome has been designed and successfully applied in bacteria (Talaat A M, Hunter P, Johnston S A, *Nat Biotechnol* 2000, 18(6):679-682).

Another lately developed method relies on a collection of short, computationally selected oligonucleotides ('not-so-random' (NSR) primers) to obtain full-length, strand-specific representation of nonribosomal RNA transcripts (Armour C D, Castle J C, Chen R, Babak T, Loerch P, Jackson S, Shah J K, Dey J, Rohl C A, Johnson J M, *Nature Methods* 2009, 6(9):647-649). Selective enrichment of non-rRNA targets was achieved by computationally subtracting rRNA priming sequences from a random hexamer library. The presence of rRNA and tRNA plagues most mRNA purification procedures due to their relative abundance, leading to non-specific interactions like rRNA adsorption to the oligo-dT matrix, or hybridization of rRNA and mRNA sequences (Matveeva O M, Shabalina S A, *Nucl Acids Res* 1993, 21:1007-1007).

What is needed in the art is a method of amplifying and quantifying selected mRNA sequences, without interference from rRNA or tRNA. The present invention is believed to be an answer to that need.

SUMMARY OF THE INVENTION

The present invention is directed to multi-targeted priming (MTP), a gene expression quantification method that allows for selective amplification of chosen sequences. In the method of the invention, a degenerate oligonucleotide complementary to selected mRNAs and absent in both rRNA or tRNA is identified allowing for selective transcription of mRNA. To demonstrate the power of the method, species-specific primers were designed and tested on RNA from *Saccharomyces cerevisiae* exposed to nitrogen deficiency, and on RNA from *Neurospora crassa* during early sexual development following nitrogen depletion. When primary nitrogen sources are not available or are present in concentrations low enough to limit growth, many different nitrogen sources can be used. Utilization of secondary nitrogen sources is highly regulated, and nearly always requires the synthesis of a set of pathway-specific catabolic enzymes and permeases (Marzluf G A, *Microbiol Mol Biol Rev* 1997, 61(1):17-32). Several studies have shown the induction of a common suite of effector genes during growth of fungal plant pathogens under nitrogen-starved conditions in vitro and during growth in planta. As a consequence, nitrogen-starved media has become a model for the environment that a pathogen encounters during growth in planta (Bolton M D, Thomma B, *Physiol Mol Plant Pathol* 2008, 72(4-6):104-110; Donofrio N M, Oh Y, Lundy R, Pan H, Brown D E, Jeong J S, Coughlan S, Mitchell T K, Dean R A, *Fungal Genet Biol* 2006, 43(9): 605-617). Furthermore, nitrogen uptake and exchange are key processes for ectomycorrhizal interactions that are established between the root systems of terrestrial plants and hyphae from soil-borne fungi (Mueller T, Avolio M, Olivi M, Benjdia M, Rikirsch E, Kasaras A, Fitz M, Chalot M, Wipf D, *Phytochemistry* 2007, 68(1):41-51; Lucic E, Fourrey C, Kohler A, Martin F, Chalot M, Brun-Jacob A, *New Phytol* 2008, 180(2):343-364). Finally, nitrogen deficiency has been associated with major problems encountered in contemporary wine making (Manginot C, Roustan J L, Sablayrolles J M, *Enzyme Microb Technol* 1998, 23(7-8):511-517), especially those related to slow and incomplete fermentations (Backhus L E, DeRisi J, Brown P O, Bisson L F, *FEMS Yeast Res* 2001, 1(2):111-125). Therefore, the response of budding yeast exposed to nitrogen starvation has been of interest in light of nutrient depletion during wine fermentation.

*Neurospora crassa* is a heterothallic filamentous fungus that undergoes a complex pattern of sexual differentiation to form the female reproductive structure (protoperithecium) when subjected to conditions of nitrogen starvation, light, and low temperature (Perkins D D, Barry E G, *Adv Genet* 1977, 19:133-285). A large number of genes affecting sexual development have been identified by mutation (Delange A M, Griffiths A J F, *Genetics* 1980, 96(2):367-378, Raju N B, *Mycol Res* 1992, 96:241-262), but large-scale transcript profiling has not been performed.

This invention results in a greater quantity of reverse transcription of a more diverse set of expressed sequences than traditional poly-T priming. Furthermore, it minimizes the creation of cDNA from highly abundant rRNAs, a minor problem for poly-T priming, but a major problem for poly-N priming. Lastly, it may be used to reverse transcribe a known subset of genomic sequences while largely avoiding reverse transcribing other sequences that may be of little to no use in the downstream application.

The results of enhanced-transcript profiling of yeast grown in nitrogen poor and nitrogen rich conditions were compared to the results obtained when ordinary technology was used (Table 1). The enhancement increased the number of well-measured genes, recorded after data normalization, by 31% (from 4620 to 6042). Among significantly differentially expressed genes, 316 were indicated exclusively by the ordinary experiment, while 1738 genes were indicated exclusively by the enhanced experiment. 1839 additional genes were identified by both approaches. Generally, genes indicated as significantly differentially expressed in one experiment but not the other had similar estimated expression levels and borderline P-values in both experiments.

The enhanced transcription was also independently incorporated into an experiment to quantify gene expression in mycelia and protoperithecia formed by the fungus *N. crassa* during growth on nitrogen-poor medium, and the results were compared with transcript profiling using ordinary reverse transcription. Application of the enhanced technology increased the number of well-measured genes by 331%, to 2022 (Table 1). The number of genes identified as significantly differentially expressed in *N. crassa* protoperithecia rose by 136%, from 172 to 406. 92 genes overlapped between the two experiments. The increase in the number of genes differentially expressed detected by the enhanced technology, as compared to results obtained with ordinary technology, affected genes that were abundantly expressed in protoperithecia (from 66 to 232) to a greater degree than it affected genes meagerly-expressed in protoperithecia (from 106 to 174). The highest and the average gene expression ratio estimated based on the enhanced experiment were lower than for data obtained with the ordinary technology (Table 1). The GEL50 value was similar when the enhancer was included compared to when the ordinary technology was used. However, 38% more genes were detected as differentially expressed in the enhanced experiment above the GEL50 threshold than were differentially expressed above the GEL50 threshold in the experiment with ordinary technology (Table 1). Thus, many more gene expression levels were precisely estimated with the enhancement, even though in this experimental case there was not a finer level of resolution for small changes in gene expression.

Accordingly, in one embodiment, the present invention is directed to a method of generating a library of expressed cDNA sequences, comprising the steps of (1) providing a listing of multiple mRNA sequences in a genome; (2) identifying one or more degenerate motifs that bind to a large proportion of the mRNA sequences; (3) providing one or more multi-targeted primers that are complementary to one or more of the degenerate motifs; and (4) combining said multi-targeted primers with said mRNA sequences in a reverse transcription assay to generate a library of expressed cDNA sequences.

In another embodiment, the present invention is directed to a method of reverse mRNA transcription, comprising the steps of (1) providing a multi-targeted primer; (2) providing an oligo-dT primer; (3) combining said multi-targeted primer and said oligo-dT primer with mRNA in a reverse transcription assay; and (4) reverse transcribing said mRNA.

These and other embodiments are described in the several figures and following detailed description of the invention.

BRIEF DESCRIPTION OF THE FIGURES

The invention will be better understood from the following detailed description of the invention taken in conjunction with the Figures, in which.

DETAILED DESCRIPTION OF THE INVENTION

Figure 2:
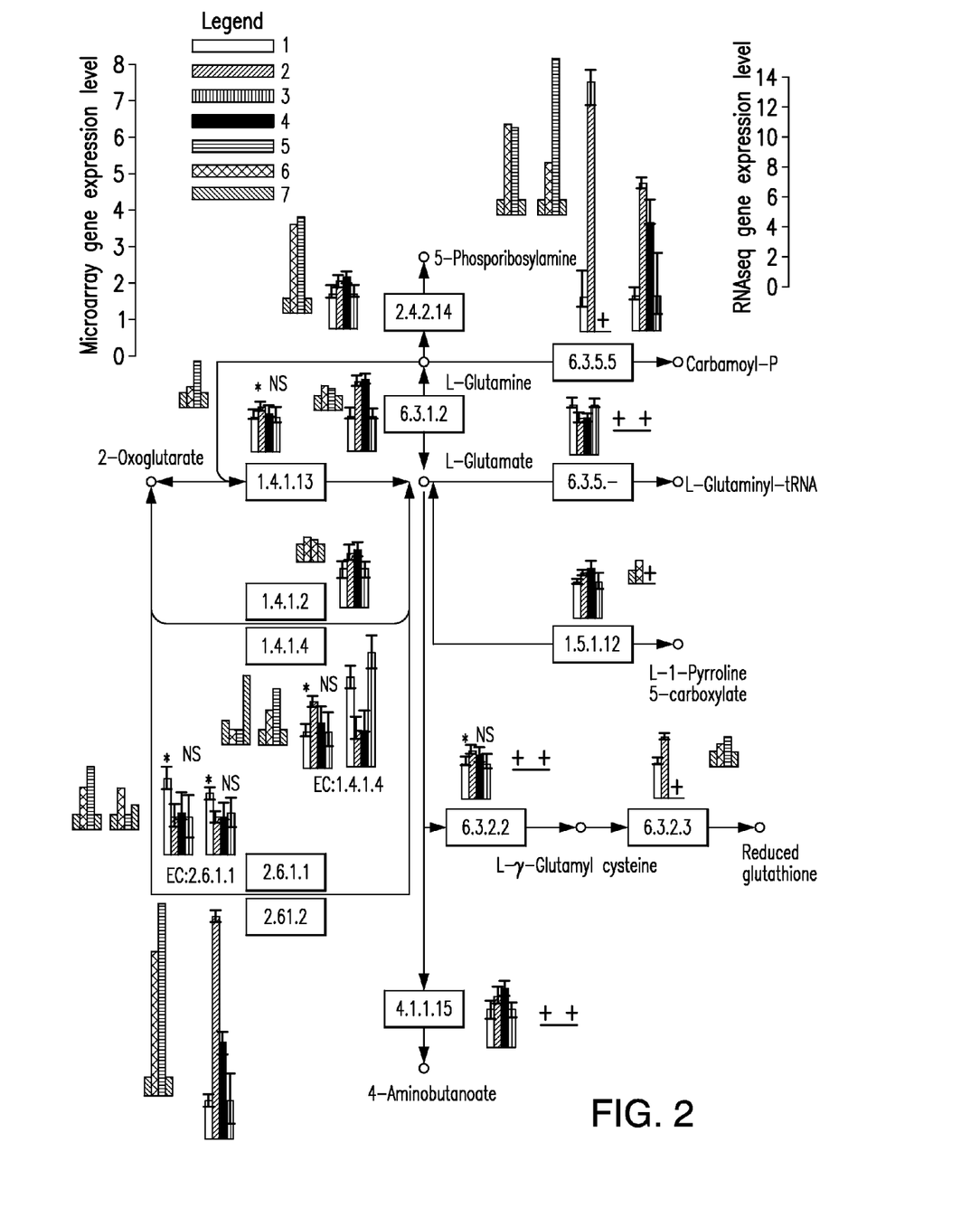
FIG. 2 is a schematic showing genes significantly differentially expressed ($P \leq 0.05$) by *S. cerevisiae* growing in nitrogen-poor (outer bars) and nitrogen-rich (inner bars) conditions coding for enzymes involved in glutamate metabolism; identified by microarray using multi-targeted primers (left bars) or oligo(dT) primers (right bars). The results were validated using RNA sequencing on Illumina platform (grey; bars in the same order as for microarray profiling). Error bars represent 95% credible intervals. NS—statistically insignificant difference ($P \geq 0.05$); * or lack of a symbol—significant difference in gene expression level ($P \leq 0.05$); † —microarray: not well measured; tag sequencing: not detected or too few tags for a statistical significance ($P > 0.05$).
Figure 3:
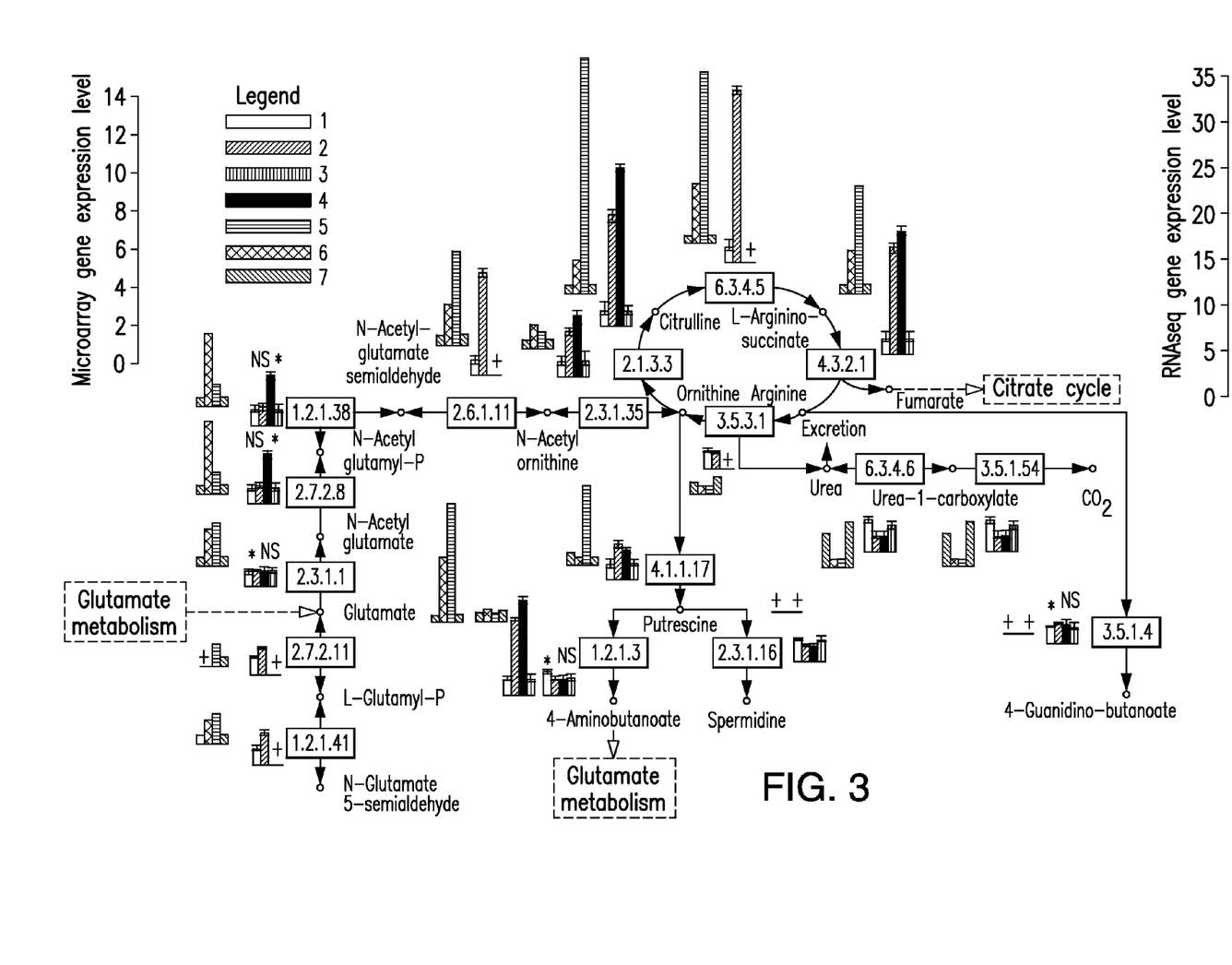
FIG. 3 is a schematic showing genes significantly differentially expressed ($P \leq 0.05$) by *S. cerevisiae* growing in nitrogen-poor (light colored bar) and nitrogen-rich (dark colored bar) conditions coding for enzymes involved in urea cycle and metabolism of amino groups; identified by microarray using multi-targeted primers (left bars) or oligo(dT) primers (right bars). The results were validated using RNA sequencing on Illumina platform (grey; bars in the same order as for microarray profiling). Error bars represent 95% credible intervals. NS—statistically insignificant difference ($P > 0.05$); * or lack of a symbol—significant difference ($P \leq 0.05$); † —not well measured.
Figure 4:
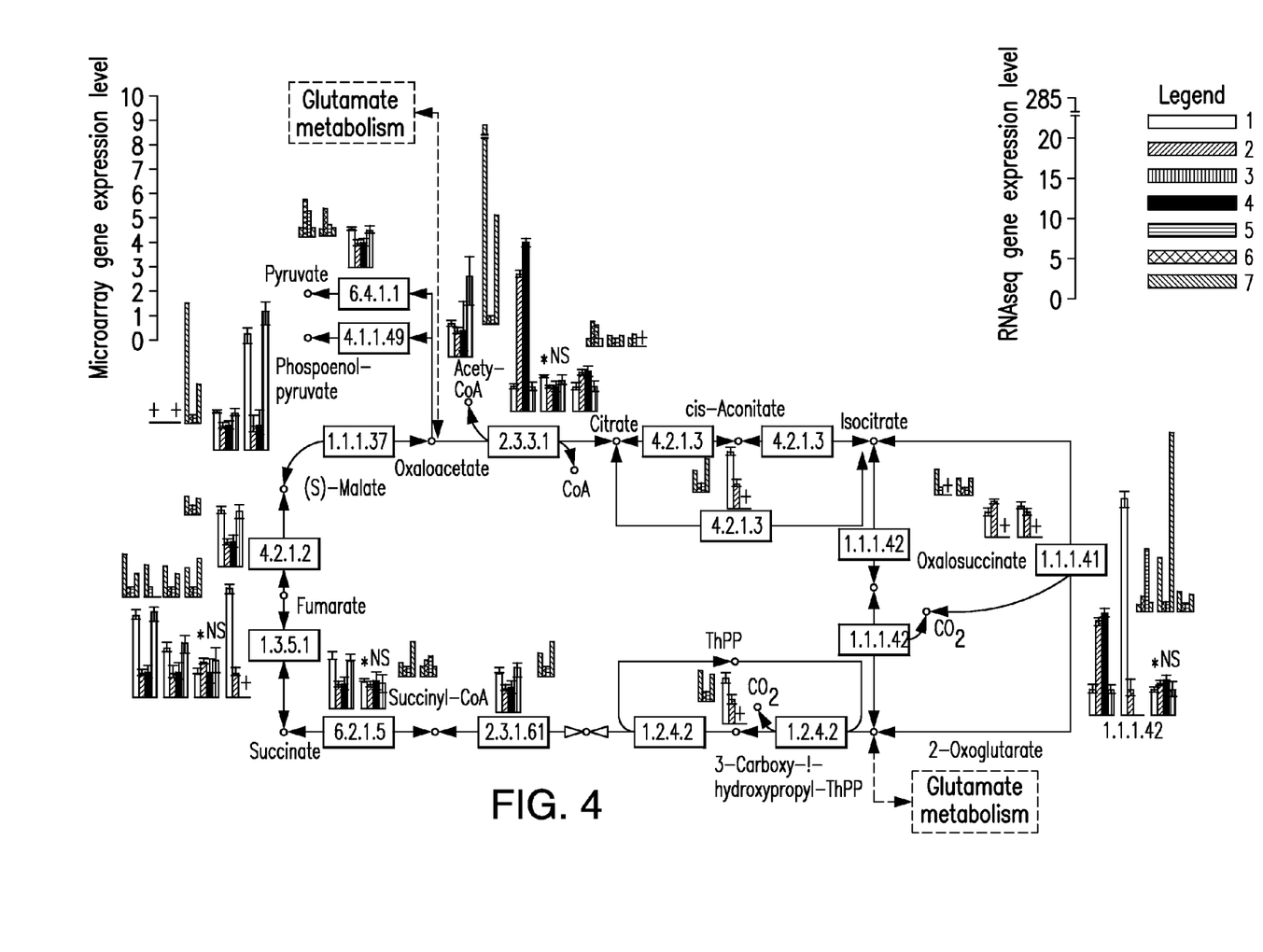
FIG. 4 is a schematic showing genes significantly differentially expressed ($P \leq 0.05$) by *S. cerevisiae* growing in nitrogen-poor (outer bars) and nitrogen-rich (inner bars) conditions coding for enzymes involved in citrate cycle (TCA); identified by microarray using multi-targeted primers (red) or oligo(dT) primers (blue). The results were validated using RNA sequencing on Illumina platform (grey; bars in the same order as for microarray profiling). Error bars represent 95% credible intervals. NS—statistically insignificant difference ($P > 0.05$); * or lack of a symbol—significant difference ($P \leq 0.05$); † —not well measured.

The multi-targeted priming method of the present invention features selective targeting of multiple genomic sequences and counter-selection against undesirable sequences. For genome-wide gene expression assays, the addition of multi-targeted primers offers the potential for improving the coverage of the reverse transcription. Reverse transcription reactions are fairly nonspecific: transcription may be primed by non-complementary primers, other RNA molecules present in the sample, and even by dNTPs, so the priming strategy selected may be expected to play a significant role in determining the results obtained. For instance, commonly-used oligo-dT primers generate a high frequency of truncated cDNAs through internal poly-A priming (Nam D K, et al., *Proc Natl Acad Sci USA* 2002, 99(9):6152-6156). In the present invention, addition of MTP to commonly used oligo-dT primers for yeast and *N. crassa* microarray profiling substantially increased the number of well measured genes recorded after data normalization as well as the number of genes significantly differentially expressed, compared with the sole use of oligo-dT primers (see Table 1). Additionally, MTP-based profiling manifested higher statistical power as demonstrated by lower value of $GEL_{50}$, a measure of empirical power to reveal differences in gene expression (Townsend J: *BMC Bioinformatics* 2004, 5(1):54), in the *S. cerevisiae* experiment.

expression levels for a higher number of genes than when priming with oligo-dT (41% and 35%, respectively; see FIGS. 2-4).

TABLE 2

Overview Of Transcriptomic Sequence Reads, Comparing Numbers of Matches to Coding ORFs, rRNAs, and tRNAs

| | Single match mRNA | Single match rRNA | Single match tRNA | Multiple matches | Unmatched |
|---|---|---|---|---|---|
| Oligo-dT N-rich | 266258 | 40 | 18 | 72849 | 258323 |
| Oligo-dT N-poor | 569310 | 38 | 12 | 99222 | 673334 |
| MTP N-rich | 1286862 | 438 | 18 | 1197105 | 1312253 |
| MTP N-poor | 1444282 | 1418 | 21 | 470558 | 1136358 |

To explain this result, note that both traditional oligo-dT and MTP priming provide biased counts and profile only a proportion of the total RNA pool. Some genes that are poorly primed by oligo-dT primers are those that have protected poly-A tails due to foldback structures; other genes, such as histones in metazoan DNA, have no poly-A tail. In a particularly clear case for yeast, it has been demonstrated that many to all of the 24 putative and known mitochondrial mRNAs are not stabilized by a poly-A tail (see, for example, Dieckmann C L, Tzagoloff A, *J Biol Chem* 1985, 260:1513-1520). For these genes, MTPs were successful at priming and revealing gene expression differences, whereas oligo-dT primers were not. Some genes feature multiple sites for priming by MTPs, leading to greater power for the detection of differential expression for those genes. However, the effect of multiple priming is modest, mostly increasing the chance of a gene being well measured. The equivalent coefficients of variation

TABLE 1

Overview of the Results Comparing Use of Oligo(dT) and Multi-Targeted Primers (MTPs) for Reverse Transcription

| | *Saccharomyces cerevisiae* Nitrogen depletion | | | *Neurospora crassa* Protoperithecial development | | |
|---|---|---|---|---|---|---|
| Feature | Oligo (dT) | MTP | Common | Oligo (dT) | MTP | Common |
| Number of well measured genes[1] on the array | 4620 | 6042 | 4573 | 469 | 2021 | 416 |
| Number of genes significantly differentially expressed (P ≤ 0.05) | 2155 | 3577 | 1839 | 172 | 406 | 92 |
| Number of up-regulated genes (P ≤ 0.05) | 1080 | 1855 | 925 | 66 | 232 | 31 |
| Number of down-regulated genes (P ≤ 0.05) | 1075 | 1722 | 912 | 106 | 174 | 61 |
| Highest gene expression ratio | 49.15 | 32.6 | | 24.26 | 10.74 | |
| Average gene expression ratio | 2.05 | 1.77 | | 1.96 | 1.43 | |
| $GEL_{50}$[2] | 1.51 | 1.27 | | 1.91 | 2.08 | |
| Number of genes with gene expression ratio greater or equal to GEL50 (P ≤ 0.05) | 1237 | 2617 | 1166 | 102 | 141 | 52 |

[1]well measured genes recorded after data normalization (foreground fluorescence signals were at least three standard deviations of the distribution of intensities of the background pixels for that gene).
[2]$GEL_{50}$—gene expression level at which there is a 50% empirical probability of a significant call.

High-throughput RNA tag sequencing was used to confirm the utility of MTPs, combined with oligo-dT column purification, for priming reverse transcription reactions, yielding an increased number of detected and well measured genes, compared to oligo-dT primers alone (see Table 2). Priming using MTPs, the inventor was able to corroborate gene expression levels for a higher number of genes than when of the transcriptomic tag sequencing runs indicate that the complexity of the mRNA pool with either priming strategy is approximately the same. The advantage of adding MTPs obtains because the reverse transcription biases for each method of priming are different. In combination, they exhibit greater coverage than either would individually. Based on high-throughput transcript sequencing data, it is believed that MTPs might yield slightly better coverage of expressed sequences than oligo-dT. In terms of false negatives in the high-throughput transcript sequencing, MTP priming exhibited a lower false-negative rate (248 not detected by MTP mix that were detected by oligo-dT alone) than did oligo-dT priming alone (368 not detected by oligo-dT that were detected by MTP). Correlations between replicate tag sequencing results and between replicate MTP-based microarray results were similar. Next generation RNA tag sequencing offers a promise of increasing power, depth, and sensitivity of gene expression analysis, but even a limited depth of RNA sequencing remains costly compared to a highly replicated experiment using microarrays generated in the lab.

Finally, qRT-PCR validated the results based on MTP-priming. It confirmed that genes identified as well measured or as significantly differentially expressed only by MTP-primed microarray, had changed in expression in the direction revealed by the MTP-primed experiments, regardless of the primer combination used. This observation suggests that incorporating MTPs increases the power for detection of differential expression by microarrays, by increasing the coverage of the priming of reverse transcription while maintaining low noise due to nonspecific priming. Logistic regressions showed some evidence that genes with more priming sites were measured with increased power with MTPs applied than genes with fewer MTP priming sites, but this observation was true (albeit to a lesser extent) for oligo-dT priming as well. This commonality may well arise because longer genes have more MTP sites and are better measured with either MTPs or oligo-dT primers. Considering the 4762 observations underlying these effects, their statistical significance is unsurprising. The effect sizes are not large. It would be possible to procedurally minimize the variation in the number of MTP sites, but effectively, this minimization of variation would entail searching for MTPs that were less powerful for some genes. That would be counter-productive to the effort to measure genome-wide gene expression for as many genes as possible to the best precision possible. Because such gene-specific effects exist at approximately the same levels no matter the method of priming, decent statistical approaches toward microarray data have featured effects estimated for each gene, thus providing P-values and confidence or credible intervals that appropriately reflect the variation in power across genes. Markedly successful enhancement of the power of transcriptomic approaches was achieved here by usage of MTPs subsequent to a crude filtration provided by poly-A+ purification columns, which typically bring the RNA content to approximately 50% poly-A+ RNA and 50% other RNA (Sambrook J, Fritsch E F, Maniatis T, *Molecular cloning*. vol. 1: Cold Spring Harbor Laboratory Press Cold Spring Harbor, N.Y.; 1989: 7.26-27.29; Kingston R: *Current Protocols in Molecular Biology*. Edited by Ausubel F M, Brent R, Kingston R E, Moore D D, Seidman J G, Smith J A, Struhl K. New York: John Wiley & Sons; 1997: 4.5.1-4.5.3). An alternate approach with potential to further increase power would be to forego any column purification of poly-A+, relying solely on MTPs to pick out messenger RNA from other species of RNA.

Figure 1A:
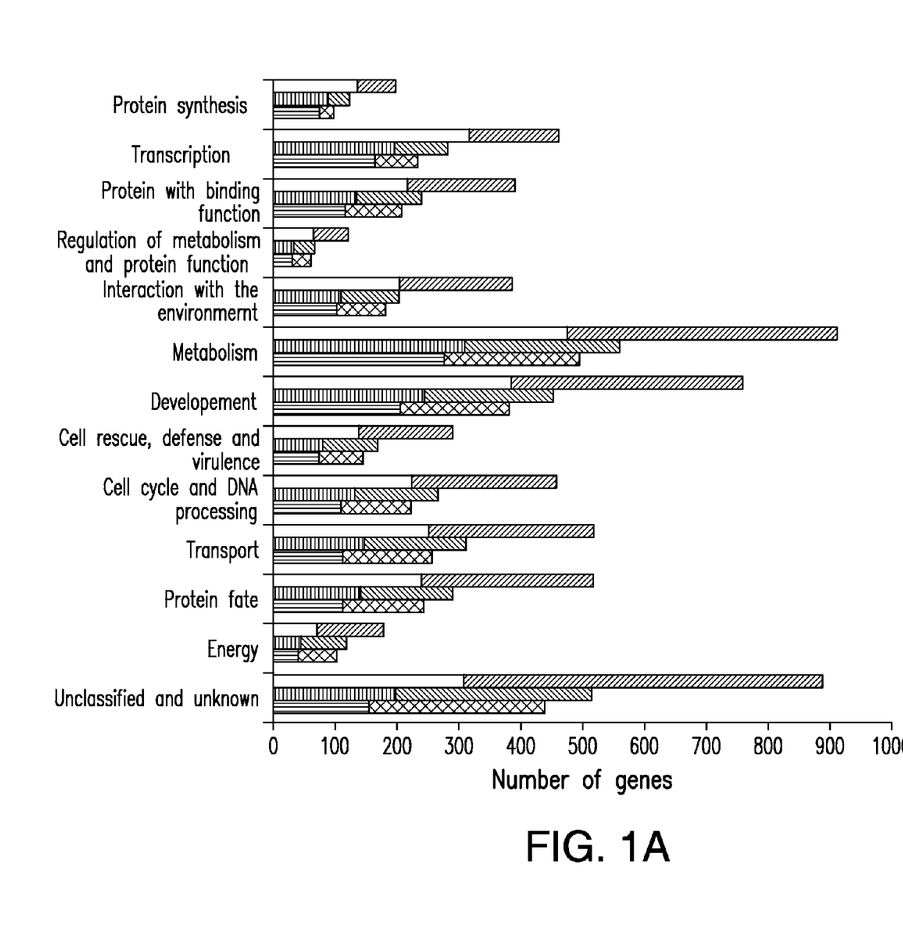
FIG. 1 is a histogram showing functional classification of genes significantly differentially expressed ($P \leq 0.05$) by a) *S. cerevisiae* grown in nitrogen-poor conditions and b) *N. crassa* protoperithecia identified by transcript profiling multi-targeted primers (top bars) or oligo(dT) (middle bars). Genes identified by both methods indicated by the lower bars. Light-colored bars represent genes meagerly expressed and dark-colored bars represent genes abundantly expressed. The categories are sorted by the proportion of genes meagerly—to abundantly—expressed.
Figure 1B:
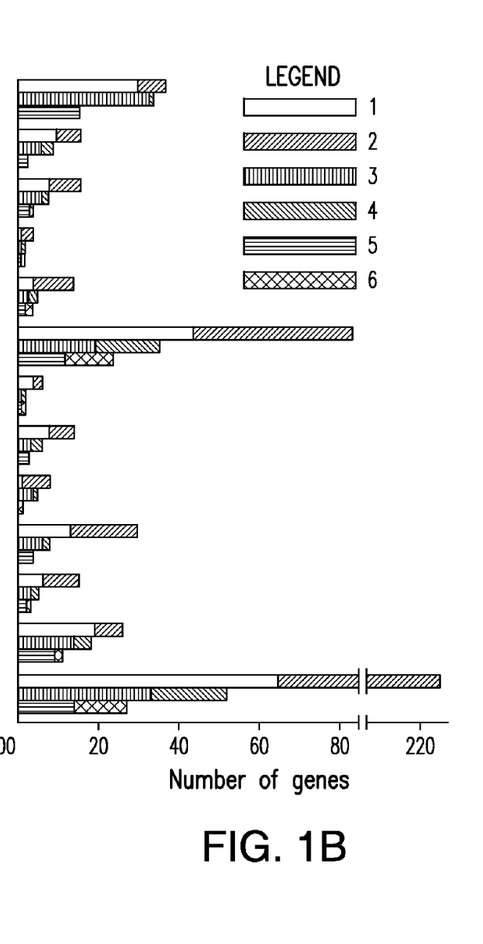

Functionally, inclusion of MTPs provided a more complete picture of cellular processes undergoing change during fungal growth in nitrogen deficient conditions and in early sexual development. One difference in the ability to detect genes differentially expressed between MTPs and oligo-dT primers was observed among *N. crassa* unknown and unclassified genes (FIG. 1*b*). Genes expressed at a low level have a lower probability of being identified and characterized than those expressed at a higher level (Wang S M, Fears S C, Zhang L, Chen J J, Rowley J D, *Proc Natl Acad Sci USA* 2000, 97(8): 4162). Only 42% of genes in *N. crassa* genome have been assigned known functions (Galagan J E, Calvo S E, Borkovich K A, Selker E U, Read N D, Jaffe D, FitzHugh W, Ma L J, Smirnov S, Purcell S et al: *Nature* 2003, 422(6934):859-868) so identifying their expression signatures and inferring functional classification are key objectives of future experimentation (Dunlap J C, et al., *Adv Genet* 2007, 57:49-96). The increased levels of yeast transcripts coding for enzymes involved in the TCA cycle observed here (FIG. 4) supports a finding that the content of TCA cycle compounds increases during yeast starvation (Brauer M J, Yuan J, Bennett B D, Lu W Y, Kimball E, Botstein D, Rabinowitz J D: *Proc Natl Acad Sci USA* 2006, 103(51):19302-19307). Both carbon and nitrogen limitation have been shown to enhance respiration relative to fermentation in yeast (Lagunas R, Dominguez C, Busturia A, Saez M J, *J Bacteriol* 1982, 152(1):19-25). Amino acid metabolism was strongly affected by exposure to nitrogen deficiency, as in the filamentous fungus *Magnaporthe grisea*. Prevalent down-regulation of glutamate metabolism pathway (FIG. 2) was in accordance with decline of total glutathione pool found in nitrogen-starved *S. cerevisiae* (Mehdi K, Penninckx M J, *Microbiology* 1997, 143: 1885-1889). Similarly, the urea cycle was down-regulated, with an exception of the branch responsible for urea degradation (FIG. 3). Urea amidolyase, the enzyme corresponding to that branch, contains both urea carboxylase and allophanate hydrolase activities. It also converts allantoin to ammonia and carbon dioxide, enabling *S. cerevisiae* to use allantoin as a sole nitrogen source (Cooper T G, Ferguson D, Rai R, Bysani N, *J Bacteriol* 1990, 172(2):1014-1018). The urea cycle operates in terrestrial animals to detoxify ammonia, and in yeast plays a principal role in the biosynthesis of arginine. Within these pathways, we were able to characterize expression of multiple isozymes and isoforms (FIGS. 2-4) providing a key component of a full understanding of expression regulation in nitrogen-deficient medium. The general trend of shutting down amino acid biosynthesis and metabolism appears essential for survival during prolonged periods of starvation. These results from our experiments are entirely consistent with a functional category analysis of independent data from the unreplicated time-course experiment by Gasch et al. (supra).

A number of genes abundantly expressed by yeast during growth in nitrogen-poor conditions are components of the environmental stress response that was characterized by evaluating the transcriptional responses to a wide range of stress stimuli, including nitrogen depletion. The remaining genes might be involved in immediate responses specific to nitrogen limitation, but many are likely associated with transitive effects that occur over time, such as successive nutrient depletion, pH change, cell density, and growth arrest. The finding that development-related genes were significantly affected in this study may be related to growth arrest or to a morphological switch from the yeast to a filamentous or pseudohyphal growth triggered by nitrogen starvation in the presence of a fermentable carbon source, such as glucose (Kron S J, Styles C A, Fink G R, *Mol Biol Cell* 1994, 5(9): 1003-1022). Nutrient and nitrogen sensing plays important roles in fungal development in general, and specifically in critical aspects of pathogenicity and virulence, for both animal and plant pathogens. Dimorphic pathogens such as the phytopathogenic smut fungi, *Ustilago maydis* and *Microbotryum violaceum*, must switch from a yeast-like to a filamentous form in order to cause disease (Smith D G, Garcia-Pedrajas M D, Gold S E, Perlin M H, *Molecular Microbiology* 2003, 50(1):259-275).

*N. crassa* protoperithecia consist of a small knot of vegetative hyphae surrounding ascogonial cells. Their formation requires extensive cell proliferation. Thus, it was not surprising to find a large proportion of differentially expressed genes involved in metabolism, especially carbohydrate metabolism (Table 3), providing energy and the robust structural components necessary for specialized cell formation.

expressed with a 22 h rhythm under the control of the circadian biological clock (Bell-Pedersen D, Shinohara M L, Loros J J, Dunlap J C: *Proc Natl Acad Sci USA* 1996, 93(23): 13096-13101). The expression of the pheromone precursor genes is mating-type specific and is under the control of the mating type locus. These genes are highly expressed in conidia and under conditions that favor sexual development (Bobrowicz P, Pawlak R, Correa A, Bell-Pedersen D, Ebbole D J, *Molecular Microbiology* 2002, 45(3):795-804).

According to the invention, the inventors found a reduced level of transcripts related to protein synthesis (FIG. 1) in both

TABLE 3

Comparison of Oligo(dT) and MTP Priming in terms of Number of Genes Significantly Differentially Expressed in Specific Biological Processes and Metabolic Pathways with the Highest Number Of Genes Significantly Differentially Expressed (P ≤ 0.05) In *S. cerevisiae* and *N. crassa*.

| Process/pathway* | Oligo(dT) | MTP | Additional genes identified by MTP | Improvement (%) |
|---|---|---|---|---|
| *Saccharomyces cerevisiae*, nitrogen depletion | | | | |
| Carbohydrate Metabolism | 136 | 208 | 72 | 53 |
| Amino Acid Metabolism | 114 | 181 | 67 | 59 |
| Lipid Metabolism | 55 | 89 | 34 | 62 |
| Metabolism of Cofactors and Vitamins | 43 | 67 | 24 | 56 |
| Energy Metabolism | 37 | 62 | 25 | 68 |
| Glycan Biosynthesis and Metabolism | 28 | 58 | 30 | 107 |
| Xenobiotics Biodegradation and Metabolism | 28 | 52 | 24 | 86 |
| Nucleotide Metabolism | 31 | 49 | 18 | 58 |
| Signalling | 19 | 39 | 20 | 105 |
| Metabolism of Other Amino Acids | 20 | 36 | 16 | 80 |
| Cell cycle | 20 | 32 | 12 | 60 |
| Biosynthesis of Secondary Metabolites | 9 | 15 | 6 | 67 |
| Folding, Sorting and Degradation | 7 | 12 | 5 | 71 |
| Replication and repair | 8 | 8 | 0 | 0 |
| Translation | 2 | 2 | 0 | 0 |
| Transcription | 1 | 1 | 0 | 0 |
| *Neurospora crassa*, protoperithecial development | | | | |
| Carbohydrate metabolism | 23 | 30 | 7 | 30 |
| Translation | 25 | 29 | 4 | 16 |
| Amino acid metabolism | 14 | 26 | 12 | 86 |
| Lipid metabolism | 8 | 19 | 11 | 138 |
| Xenobiotics biodegradation and metabolism | 5 | 17 | 12 | 240 |
| Metabolism of other amino acids | 3 | 11 | 8 | 267 |
| Metabolism of cofactors and vitamins | 3 | 10 | 7 | 233 |
| Energy metabolism | 9 | 8 | −1 | −11 |
| Glycan biosynthesis and metabolism | 0 | 5 | 5 | ** |
| Nucleotide metabolism | 1 | 4 | 3 | 300 |
| Biosynthesis of secondary metabolites | 2 | 3 | 1 | 50 |
| Signalling | 1 | 1 | 0 | 0 |
| Protein fate | 0 | 1 | 1 | ** |
| Transcription | 0 | 1 | 1 | ** |

*The pathways and processes were identified using Kyoto Encyclopedia of Genes and Genomes (KEGG).
** biological process not identified by oligo(dT) primers as including any genes significantly differentially expressed by *N. crassa* protoperithecia.

Figure 5:
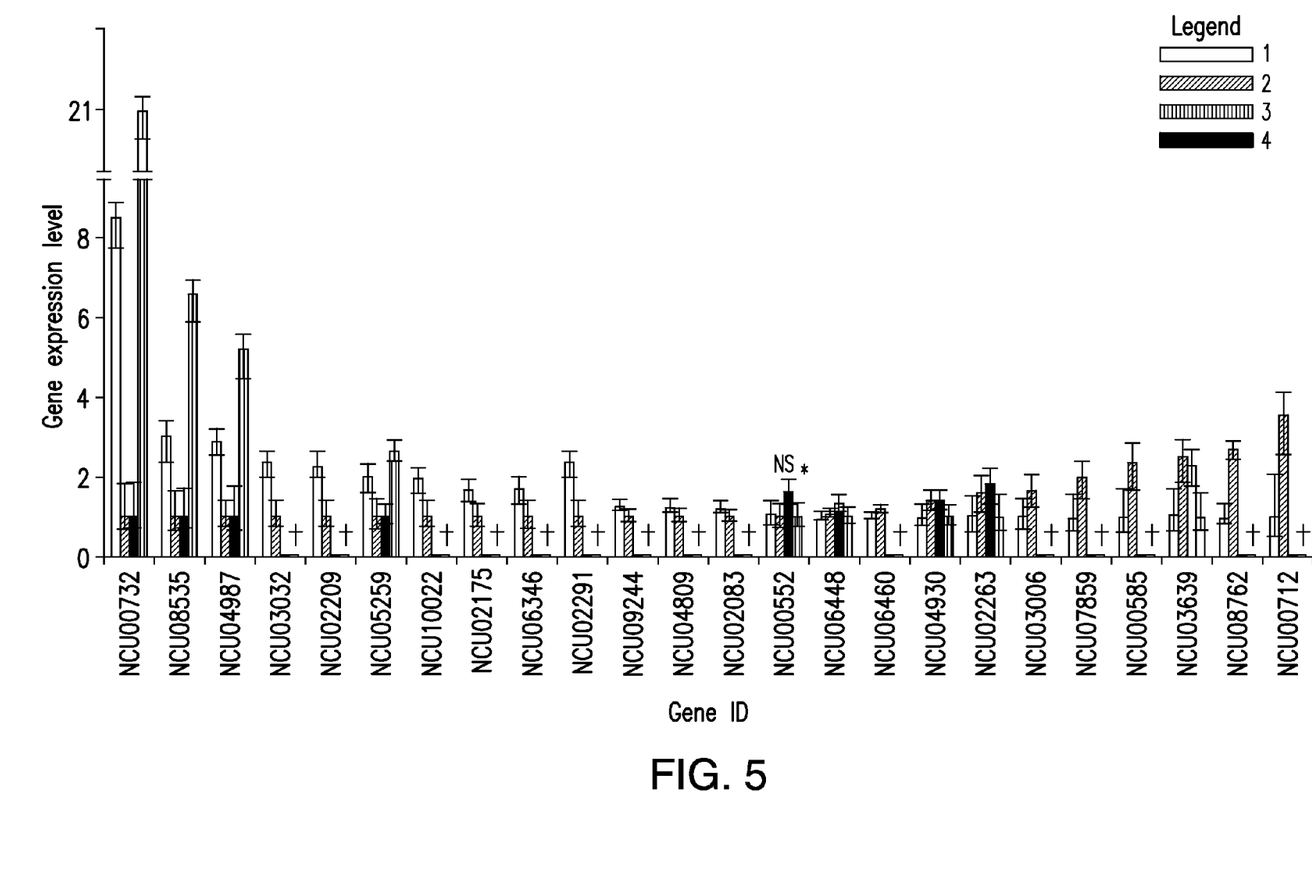
FIG. 5 is a histogram showing genes significantly differentially expressed ($P \leq 0.05$) by *N. crassa* protoperithecia (outer bars) and mycelium (inner bars) coding for enzymes involved in fatty acid metabolism; identified by microarray using multi-targeted primers (left bars) or oligo(dT) primers (right bars). Error bars represent 95% credible intervals. NS—statistically insignificant difference (P>0.05); * or lack of a symbol—significant difference (P≤0.05); † —gene not well measured.

The shift in transcript accumulation of genes involved in fatty acid metabolism (FIG. 5) supports previous observations that the fatty acid composition of sexual tissues of *Neurospora* differ substantially from the composition of asexual tissues. For instance, mutations in the gene encoding the b-fatty acid synthase affect sexual development (Goodrich-Tanrikulu M, Howe K, Stafford A, Nelson M A, *Microbiology* 1998, 144:1713-1720.). On the other hand, it was expected to identify known developmental genes responsible for the formation of protoperithecial reproductive structures, but the number of genes significantly differentially expressed involved in the functional category of development was very low. One of them coded for clock controlled pheromone ccg-4 precursor which had been first identified as a gene that is

*S. cerevisiae* under nitrogen starvation and in *N. crassa* sexual development occurring as a developmental response to nitrogen depletion. Ribosome biogenesis and protein translation are among the most energy-consuming cellular processes (Warner J R, *Trends Biochem Sci* 1999, 24(11):437-440). Thus, these pathways are tightly controlled upon nutrient limitation. Decreasing levels of protein, RNA and soluble aminonitrogen were observed during protoperithecia development as early as 1975 (Viswanath-Reddy M, Turian G, *Physiol Plant* 1975, 35(2):166-174). Additionally, ribosomes are rapidly degraded by autophagy upon nutrient starvation in *S. cerevisiae*, implying that degradation of excessive ribosomes may help to shut down protein translation rapidly and provide an important source of new building blocks to maintain cellular homeostasis (Kraft C, Deplazes A, Sohrmann M, Peter M, *Nat Cell Biol* 2008, 10(5):602-610).

The MTPs according to the present invention were designed to prime 76-85% of mRNAs rather than all the genes, so that reverse transcription of rRNA and tRNA could be simultaneously minimized. An additional step of primer design could be conducted to specifically target the remaining sequences to eliminate or further diminish the need to rely on low-complexity, low-specificity oligo-dT primers. For transcript profiling in prokaryotes, such a tiered approach would constitute an appealing alternative to the use of non-specific random primers. Correspondingly, the modification of Illumina massively parallel RNA tag sequencing presented here, involving the use of custom primers, presents the possibility of performing Digital Gene Expression assays on transcriptomes lacking poly(A) tails or on a designable fraction of all the genes. Furthermore, future applications of multi-targeted primers may include concurrent selective amplification of DNA sequences of interest from one or multiple genomes for the high-throughput sequencing of multiple homologous loci. Locked nucleic acid nucleotides could be included in the MTP sequence to increase binding strength and specificity, and to decrease non-specific amplification (Malgoyre A, Banzet S, Mouret C, Bigard A, Peinnequin A, *Biochem Biophys Res Commun* 2007, 354(1):246-252).

The present invention may be used to produce a highly representative cDNA set for the purpose of competitive hybridization, e.g. for producing labeled cDNA to be competitively hybridized on a DNA microarray. Applications of particular importance include preparation of cDNA for prokaryotes, whose expressed transcripts lack poly-A tails, and preparation of cDNA to include sequence complementary to metazoan histone transcripts or yeast mitochondrial gene transcripts, that also lack poly-A tails.

The present invention may also be used to produce a highly representative cDNA set for the purpose of establishing an in vitro library of expressed sequences, e.g. cloning expressed sequence fragments into *E. coli*.

The present invention may also be used to produce a highly representative cDNA set for the purpose of direct sequencing and/or identification of expressed sequences, e.g. Serial Analysis of Gene Expression, EST sequencing, or high-throughput sequencing of expressed sequences, using traditional or any of a variety of modem high-throughput techniques.

The present invention may also be used to produce cDNA from a particular subset of genomic expressed sequences, by modifying the "include" and "exclude" sequence lists used for the optimization of the designed primers or degenerate primers. For example, for sequencing of cDNAs of specific sets of genes to assay for mutations in a research or clinical setting; or to produce cDNAs for sequencing from genes known to have few problems with paralogy; or that would be especially phylogenetically informative.

EXAMPLES

Materials and Methods

Multi-Targeted Primers (MTPs)

Sequences for all three types of RNA were obtained from the *Saccharomyces* Genome Database (Issel-Tarver L, et al., *Methods Enzymol* 2002, 350:329) and the *Neurospora crassa* Genome Database (Galagan J E, et al., *Nature* 2003, 422 (6934):859-868). To identify a degenerate sequence that occurs in a maximal number of mRNAs and in a minimal number of tRNAs and rRNAs, exhaustive search is not a feasible option as there are $16^{12}$ such degenerate sequences. A heuristic search started with a random degenerate 12-mer oligonucleotide. Iteratively, this oligonucleotide was randomly mutated and a score was computed as $$\text{Score} = \frac{mRNAhits}{\# \ mRNAs * (1 + tRNAhits + rRNAhits)}.$$

In the above formula, mRNAhits, tRNAhits, and rRNAhits are the number of hits of the degenerate sequence to the annotated mRNAs, tRNAs, and rRNAs, and #mRNAs is the total number of annotated mRNAs. If a randomly generated number (0-1) was smaller than the ratio of the new score to the previous, raised to the power of ten, then the new oligonucleotide was kept. Otherwise, it was discarded. This procedure was iterated so that the oligonucleotide experienced $2*10^6$ mutations before the search was terminated. To ensure convergence upon a globally optimal priming sequence, several different random initial sequences were used.

Each new oligonucleotide obtained was recorded. From the ranked list, a high-scoring sequence was selected that additionally showed strong binding (GC) in the 3' end. The MTP primer was designed to be reverse-complementary to the selected dodecanucleotide.

Yeast Strain and Conditions

*Saccharomyces cerevisiae* S288c was grown in synthetic complete medium (SC) at 30° C. shaking at 160 rpm until mid log phase ($OD_{600}$=0.4). For nitrogen depletion, cells were collected and resuspended in an equal volume of minimal medium without amino acids or adenine and with limiting concentrations (0.025%) of ammonium sulfate. Cultures were harvested after 12 h incubation, flash frozen in liquid nitrogen and stored at −80° C.

Sample Preparation and Hybridization to Yeast Microarrays

A set of clones containing 6,188 verified open reading frames (ORFs) from the *Saccharomyces* Genome Project was amplified by PCR and the DNA was spotted on CMT-GAPS 7-aminopolysilane-coated glass slides (Corning, Corning, N.Y.). RNA was extracted and cDNA synthesized as in Townsend et al. (*Mol Biol Evol* 2003, 20(6):955-963). Briefly, two µg of purified mRNA were reverse transcribed using the reverse transcriptase Superscript II (Invitrogen, Carlsbad, Calif.) for 2 h at 42° C. The reaction was primed with either 0.5 µg oligo-dT primers or 0.25 µg oligo-dT mixed with 0.25 µg of yeast-specific MTP Amino-allyl-dUTP (Sigma) was incorporated into cDNA along with dNTPs. The cDNA was labeled reciprocally with cyanine dyes and used for hybridization as Townsend et al. (supra). The cDNA from yeast cultured in nitrogen-rich and the cDNA from yeast cultured in nitrogen-depleted medium were reciprocally labeled and competitively hybridized. All replicates originated from independent reverse transcription reactions.

Data Acquisition and Analysis

Hybridized microarrays were scanned and gridded with a GenePix 4000B microarray scanner (Axon Instruments, Foster City, Calif.), normalized by background-subtracted mean-by-mean normalization of well measured spots (Townsend et al., supra; Mewes H W et al., *Nucl Acids Res* 2002, 30(1):31-34), and statistically analyzed using a Bayesian analysis of gene expression levels (BAGEL, Townsend J P, Hartl D, *Genome Biol* 2002, 3(12):research0071.0071-0071.0016). Fluorescence intensity values were adjusted by subtracting background from foreground. A gene was considered well measured if the foreground fluorescence signals were higher than three standard deviations of the distribution of intensities of the background pixels for that gene. Genes were deemed significantly differentially expressed when P≤0.05. To assess the power of the experiments to detect smaller differences in gene expression, the gene expression level at which there was a 50% empirical probability of a significant call ($GEL_{50}$) was inferred by logistic regression of statistical significance against fold-change (Townsend J: *BMC Bioinformatics* 2004, 5(1):54). Functional annotation was performed based on the *Saccharomyces* Genome Database (supra) and Kyoto Encyclopedia of Genes and Genomes (KEGG) (Kanehisa M, Goto S, *Nucl Acids Res* 2000, 28(1):27-30). Significance of abundantly differentially expressed functional categories was calculated using a Fisher's exact test.

Transcriptional Tag Sequencing of Yeast in Nitrogen-Poor Conditions

Digital Gene Expression (DGE) measurement was performed using Tag Profiling with DpnII Sample Prep Kit (Illumina, San Diego, Calif.). Oligo-dT priming was performed as instructed using 2.5 µg of the same total RNA that was extracted from *S. cerevisiae* for microarrays. For multi-targeted priming, mRNA was purified on Oligo-dT Cellulose Columns (Molecular Research Center, Cincinnati, Ohio) and 2 µg were used for reverse transcription with 0.5 µg 5'-amine yeast-specific MTP and 5 mC dNTP 10 mM each (Illumina). The resulting first strand cDNA was cleaned with Microcon-30 microconcentrators and coupled to a magnetic carboxylate microparticles (Seradyn, Indianapolis, Ind.). cDNAs was immediately subjected to second strand synthesis and sequencing library preparation with the Illumina kit. Samples were then sequenced on an Illumina Genome Analyzer II.

Transcript Tag Analysis

The DGE protocol used generates 16-17 nt tags ligated to adapters. RNA sequencing produced reads of 28 bp. After discarding the included adapter sequence, perfect matches of the tag sequence in the *S. cerevisiae* genome were searched. Statistical significance was calculated by estimating the proportion p of tags per gene by maximum likelihood (maximizing $p^n (1-p)^{N-n}$ where n is the number of tags observed for the gene and N is the total number of tags for all genes), and comparing the likelihood of the observed numbers of tags with a single maximum likelihood proportion for both samples (p) to the likelihood of the observed numbers of tags with two independent maximum likelihood proportions ($p_1$ and $p_2$, one for each sample). To estimate P-values, negative two times the log likelihood ratio was compared to a chi-square distribution with one degree of freedom.

Real Time RT-PCR Validation of Yeast Microarray and RNA Sequencing Results

To validate results of yeast microarrays and RNA sequencing, ten genes were selected whose expression was well measured in the MTP-based experiment, but not well measured or insignificant in the oligo-dT experiment. An equal amount (2 µg) of mRNA, as had been used for microarray profiling, was reverse transcribed with Superscript II reverse transcriptase (Invitrogen, Carlsbad, Calif.) and 0.25 µg oligo-dT mixed with 0.25 µg yeast-specific MTP or 0.5 µg oligo-dT. Relative transcript abundance was measured using gene specific primers and SYBR Green PCR Master Mix (Applied Biosystems, Carlsbad, Calif.). The reaction was run on Applied Biosystems 7500 Fast Real-Time PCR System according to manufacturer's recommendations. A gene coding for mitochondrial ribosomal protein of the small subunit (YDR175C), whose expression did not change in the microarray experiment, was used as endogenous control. Transcript levels were calculated from triplicates within one plate using the comparative $C_T$ ($\Delta\Delta C_T$) method (ABI application notes, Guide to Performing Relative Quantitation of Gene Expression Using Real-Time Quantitative PCR).

Induction of *Neurospora crassa* Sexual Development

*Neurospora crassa* (mat A) obtained from Fungal Genetics Stock Center (strain 2489) was grown on nitrogen-poor synthetic cross medium (SCM) agar plates with 1.5% sucrose as carbon source, at room temperature under natural light. The mycelium was flash frozen by application of liquid nitrogen, then harvested after 18 hours growth. Protoperithecia were similarly harvested, after 6 days.

Transcript Profiling of *Neurospora crassa* Protoperithecia

Total RNA was extracted from homogenized frozen tissue and mRNA was purified with TRI REAGENT and Oligo-dT Cellulose Columns (Molecular Research Center). Reverse transcription, data acquisition and analysis were conducted as for *S. cerevisiae*. The cDNAs were hybridized (Clark A T, Guilmette J M, Renstrom D, Townsend J P, Fungal Genet Rep 2008, 55:18-28) to whole-genome-spotted 70-mer *N. crassa* microarrays (Kasuga T, et al., *Nucl Acids Res* 2005, 33(20): 6469-6485). Samples from *N. crassa* mycelia and protoperithecia were competitively hybridized. Each experiment consisted of a dye-swap and an additional replicate hybridization. Functional classification was based on MIPS *Neurospora crassa* Genome Database and KEGG (supra).

Results

Transcript Profiling of *S. Cerevisiae* Grown in Nitrogen-Poor Conditions

A 12-nucleotide (nt) degenerate sequence was identified that occurs one or more times in 76% of 6608 mRNAs present in budding yeast, *Saccharomyces cerevisiae*, but that is absent in rRNA or tRNA. The corresponding degenerate primer was NDKTBBBBDWGS (SEQ ID NO:1). Among the 5039 yeast ORFs containing the identified degenerate sequence, 86% featured one to five exact priming sites and the remaining sequences featured six to 44 priming sites. On average, there were 3.2 priming sites per gene. Priming for reverse transcription is not highly specific, thus MTPs may prime nearly all genes with some frequency. Nonetheless, the MTP and an equal proportion of oligo-dT primers were supplied for the reverse transcription step during the microarray target labeling procedure, to achieve the greatest coverage possible.

Contrasting yeast grown in nitrogen-poor and nitrogen-rich conditions, priming by MTP increased number of well measured genes, recorded after data normalization, by 31% over oligo-dT priming (Table 1). A logistic regression indicates that a model featuring the number of MTP binding sites in a gene is a statistically significantly better predictor of whether a statistically significant difference in expression will be observed when using MTPs than is a model without a slope with regard to number of MTP binding sites (P<0.0001, slope 0.05). However, a model featuring the number of MTP binding sites is also a statistically significant predictor of the probability of a statistically significant call when oligo-dT alone is used (P=0.02, slope 0.03). More saliently, use of the MTP increased the number of genes that were identified as significantly differentially expressed by 66%.

The frequency of MTP priming sites among genes identified as significantly differentially expressed in nitrogen-depleted yeast was analyzed. Out of 1738 genes indicated by MTPs exclusively as differentially expressed, 342 did not have an MTP recognition site and 1396 genes contained one to 29 priming sites. Among 316 genes exclusively identified by oligo-dT primers as significantly differentially expressed in response to nitrogen depletion, 68 did not contain an MTP recognition site and 248 exhibited one to 18 priming sites. For the genes with the highest number of priming sites, the gene expression levels calculated based on the MTP experiment were similar to the oligo-dT experiment and typically yielded ratios close to one, indicating that a higher number of exact MTP priming sites per se did not increase detection of significant gene expression differences.

The ratio of genes abundantly expressed to genes meagerly expressed was largely unchanged when MTPs were used (Table 1). Just two genes manifested a statistically significant opposite direction of differential expression in the MTP-microarray dataset compared to both the oligo-dT dataset and the independent RNA-Seq datasets (YDR179W-A, YKL203C). Out of 3577 genes detected as significantly differentially expressed by MTP-microarray, this is a very small number and may be reasonably attributed to experimental error in the MTP-primed reverse transcription and hybridizations. The highest and average changes in gene expression level were lower for MTP than for oligo-dT (Table 1). Lastly, the gene expression level at which there was a 50% empirical probability of a significant call ($GEL_{50}$), illustrating the statistical power of the experiment, demonstrated greater resolution for MTP than for oligo-dT primers (Table 1). Three times more genes were detected as differentially expressed in the MTP experiment above its $GEL_{50}$ threshold than were differentially expressed above the $GEL_{50}$ threshold of the experiment performed with oligo-dT primers alone (Table 1).

Functional Classification of Genes Differentially Expressed by S. Cerevisiae Grown in Nitrogen-Poor Conditions While meager expression in nitrogen-poor medium was typical for genes functioning in protein synthesis and transcription, abundant expression was typical for genes coding for proteins involved in energy and genes of unknown function (FIG. 1a). This result was obtained both with the aid of MTPs and with oligo-dT primers. Using oligo-dT primers, functional categories of metabolism, development, and energy were identified as significantly affected under nitrogen deficiency (Fisher's Exact test, P=0.01, P=$2.3 \times 10^{-21}$, P=0.01). The MTP experiment identified the same functional categories, and provided additional experimental power, also identifying genes involved in regulation with the environment (P=$4.9 \times 10^{-5}$). The classification for which the highest number of genes was indicated as significantly differentially expressed by either approach was metabolism. Within metabolism, the greater power of the MTP experiment provided a stronger signal of subcategory, as more measurements were statistically significant: 39% as indicated by MTP and 15% as indicated by oligo-dT primers were involved in amino acid metabolism; 36% and 15%, respectively, in carbohydrate metabolism; and 16% and 6% in lipid metabolism.

MTPs were not biased for inference in particular pathways or processes, providing an even increase in power across all of them. For nearly every pathway or process, the microarrays performed with MTPs resulted in a more complete assessment of expression of proteins/enzymes building a pathway, assigning expression to more genes than the oligo-dT-primed experiment in each process (Table 3). Most of the genes coding for enzymes belonging to 26 pathways specifically related to nitrogen and amino acid metabolism and biosynthesis were meagerly expressed by yeast growing in nitrogen-poor conditions, e.g. glutamate metabolism and urea cycle (Table 3, FIGS. 2-3). An opposite tendency of abundant expression in nitrogen-poor conditions was observed among genes encoding proteins composing energy-related pathways, e.g. the citrate cycle (FIGS. 1 & 4). Typically, enzymes catalyzing reactions occurring in opposite directions exhibited opposite regulation (FIG. 2). Furthermore, we were able to more reliably characterize the expression of multiple genes coding for isozymes, isoforms with different cellular location and enzyme subunits (FIGS. 2-4).

A total of 561 genes identified as differentially expressed by the MTP experiment and 364 genes identified as differentially expressed by the oligo-dT experiment belonged to environmental stress response genes that were inferred by evaluating the transcriptional responses to a wide range of stress stimuli, including nitrogen depletion.

RNA Sequencing for Assessment of Transcript Abundance in S. Cerevisiae Under Nitrogen Deficiency To validate the microarray profiling results, RNA tag sequencing was performed with a modified Digital Gene Expression protocol that facilitated use of our custom oligonucleotide primers. $6.0 \times 10^5$ 16-17 bp tags for yeast grown in nitrogen-rich conditions were sequenced, primed with oligo-dT, out of which $2.7 \times 10^5$ exactly matched a single mRNA sequence in the S. cerevisiae genome. Similarly, $1.3 \times 10^6$ tags from nitrogen deprived yeast were sequenced, primed with oligo-dT, including $5.7 \times 10^5$ tags with an exact single match. $3.8 \times 10^6$ and $1.3 \times 10^6$ tags were sequenced, respectively, from yeast grown in nitrogen-rich conditions that had been MTP-primed; and $3.1 \times 10^6$ and $1.4 \times 10^6$, respectively, for yeast deprived of nitrogen that had been MTP-primed. The MTP-primed sequencing yielded larger numbers of reads in all categories. The proportion of reads mapping to rRNAs and tRNAs was slightly increased with MTPs, but with both oligo-dT and MTP priming this proportion was negligible (<0.01% of all single matches, Table 2). MTPs also did not prime a less complex pool of mRNAs than do oligo-dTs. The coefficients of variation in number of tags across genes for the oligo-dT runs were 4.3 and 3.0, and the coefficients of variation for number of tags across genes for the MTP runs were 3.3 and 3.9, so that the pool of transcriptomic tag sequences returned when priming with MTPs were no more rarified than the pool of transcriptomic tag sequences returned when priming with oligo-dT.

A higher number of well-measured genes for the MTP-based dataset were identified than for the oligo-dT data (Table 4). In comparison to the significantly differentially expressed gene list from microarray profiling of yeast using oligo-dT primers, tag sequencing confirmed 35% of the genes with gene expression levels consistent between the two methods of measuring transcript abundance, but left 57% of the genes without statistically significant confirmation (FIGS. 2-3). In comparison to the MTP-primed microarray experiment, MTP-based tag sequencing confirmed 41% of the results, leaving 48% without statistically significant confirmation (FIGS. 2-4). Differences in the functional category of metabolism were validated. In particular, MTP identified 13 out of 24 mitochondrially encoded genes as statistically significantly differentially expressed. Oligo-dT identified none. Oligo-dT priming led to fewer than six tags in both conditions for 22 out of 24 mitochondrial ORFs. In contrast, with MTP, only nine ORFs show fewer than six tags. Furthermore, of those nine, five are considered dubious ORFs anyway.

TABLE 4

Overview Of Differential Expression From Transcriptomic Tag Sequencing, Comparing Results Of Oligo-dT and Multi-Targeted Primers (MTPs) for Reverse Transcription

| Feature | Saccharomyces cerevisiae Nitrogen Depletion | | |
|---|---|---|---|
| | Oligo-dT | MTP | Common |
| Recorded Genes | 4858 | 5078 | 4710 |
| Genes significantly differentially expressed ($P \leq 0.05$) | 2272 | 2861 | 1437 |
| Up-regulated genes ($P \leq 0.05$) | 958 | 1437 | 522 |

TABLE 4-continued

Overview Of Differential Expression From Transcriptomic Tag Sequencing, Comparing Results Of Oligo-dT and Multi-Targeted Primers (MTPs) for Reverse Transcription

| Feature | Saccharomyces cerevisiae Nitrogen Depletion | | |
|---|---|---|---|
| | Oligo-dT | MTP | Common |
| Down-regulated genes ($P \leq 0.05$) | 1314 | 1427 | 633 |
| Highest gene expression ratio | 166 | 284 | |
| Average gene expression ratio | 1.84 | 1.90 | |

Quantitative RT PCR Validation of Microarray Profiling and Tag Sequencing of Yeast Grown in Nitrogen-Poor Conditions To validate results of microarray and RNA sequencing using MTP, quantitative reverse transcription PCR (qRT-PCR) was performed (Table 5). Five genes were selected that were well measured by the microarray-MTP dataset but that did not produce enough signal in the microarray-oligo-dT dataset to be measured, and that showed the largest differences in expression between samples. In all five of these genes, differential expression in the direction predicted by the microarray-MTP dataset and the RNA-seq dataset was validated. Five genes were also selected that showed the largest, statistically significant differences in the dataset of microarrays primed with MTPs, but that due to lower power showed no statistically significant difference in the dataset of microarrays primed using oligo-dT. In four of these five genes, differential expression in the direction predicted by the microarray-MTP dataset and the RNAseq dataset was confirmed. In the one exception, the qRT-PCR result contradicts the directional trend of all four previous measurements (microarray-MTP, microarray-oligo-dT, RNAseq-MTP, and RNAseq-oligo-dT). Genes that were well measured in both array experiments but that were statistically significant due to the increased power of the MTP-based profiling had generally exhibited fairly low fold changes. Similarly low differences in expression in the same direction were detected by qRT-PCR, confirming the validity of MTP approach.

ID NO:2) was reverse complementary to 12-nt sequences found one or more times in 85% of the predicted mRNAs, one time in one tRNA, and one time in one rRNA. The MTP was incorporated into an experiment to quantify gene expression in mycelia and protoperithecia formed by the fungus during growth on nitrogen-poor medium, and the results were compared with transcript profiling using solely oligo-dT-based reverse transcription. Application of multi-targeted primers increased the number of well-measured genes by 331% (Table 1). The number of genes identified as significantly differentially expressed in N. crassa protoperithecia rose by 136%. The highest and the average gene expression ratio estimated based on the MTP-based experiment were lower than for data obtained with only oligo-dT primers (Table 1). The $GEL_{50}$ value was similar when MTPs were included, compared to when only oligo-dT primers were included. However, 38% more genes were detected as differentially expressed in the MTP experiment above the $GEL_{50}$ threshold than were differentially expressed above the $GEL_{50}$ threshold in the experiment primed with oligo-dT primers alone (Table 1). Thus, more gene expression levels were precisely estimated with MTPs, even though in this case there was not a finer level of resolution for small changes in gene expression.

Functional Classification of Genes Significantly Differentially Expressed by N. crassa Protoperithecia Within each of the functional groups of protein synthesis, transcription, energy, and genes of unknown function, a higher proportion of genes were meagerly expressed in N. crassa protoperithecia than were abundantly expressed (FIG. 1b). While the functional classifications with the highest number of genes significantly differentially expressed in protoperithecia were the "unknown" functional category or were metabolism-related, the oligo-dT-primed experiment indicated that genes involved in protein synthesis were significantly affected by sexual development (Fisher's Exact test, $P=2 \times 10^{-6}$). Application of MTPs for N. crassa microarray profiling additionally identified the functional categories of metabolism (P=0.003) and energy (P=0.03) as including a higher proportion of genes differentially expressed in protoperithecia. Enzymes involved in fatty acid metabolism were frequently abundantly expressed in N. crassa protoperithecia as compared to mycelia (FIG. 5), while genes coding for

TABLE 5

Validation Of Microarray and RNA Sequencing of Yeast Grown in Nitrogen Poor (MM) and Nitrogen Rich (SC) Conditions using Real Time (RT) PCR.

| | Microarray | | | | RNA sequencing | | | | RT PCR | |
|---|---|---|---|---|---|---|---|---|---|---|
| | MTP | | oligo(dT) | | MTP | | oligo(dT) | | MTP | Oligo(dT) |
| Gene ID | Ratio MM/SC | p value | Ratio MM/SC | p value | Ratio MM/SC | p value | Ratio MM/SC | p value | Ratio MM/SC | Ratio MM/SC |
| YDL244W | 1.98 | 0.00 | | | 3.16 | 0.11 | | | 28.94 | 39.62 |
| YGR225W | 1.72 | 0.00 | | | 7.65 | 0.00 | | | 4.08 | 3.13 |
| YGR249W | 1.66 | 0.01 | | | 5.80 | 0.00 | | | 4.79 | 8.20 |
| YMR025W | 1.51 | 0.00 | | | 3.96 | 0.15 | | | 2.10 | 1.57 |
| YNR072W | −1.24 | 0.05 | | | −6.32 | 0.00 | | | −2.34 | −1.36 |
| YFR034C | −1.42 | 0.02 | −1.25 | 0.10 | −9.08 | 0.00 | −6.41 | 0.08 | 1.30 | 1.24 |
| YKR053C | −5.37 | 0.00 | −1.88 | 0.14 | −2.16 | 0.00 | 1.15 | 0.51 | −2.10 | −2.05 |
| YLR126C | 1.54 | 0.00 | 1.36 | 0.11 | 5.54 | 0.05 | 1.40 | 0.42 | 1.58 | 1.95 |
| YMR003W | 1.25 | 0.01 | 1.11 | 0.26 | 7.91 | 0.01 | 2.65 | 0.08 | 1.03 | 1.95 |
| YOR252W | 1.29 | 0.01 | 1.03 | 0.46 | 6.33 | 0.00 | 1.54 | 0.10 | 1.99 | 1.54 |

Microarray mRNA Profiling of Neurospora crassa Undergoing Sexual Development

The MTP for the N. crassa was designed targeting 9846 protein-coding ORFs. Sequence VWNVNNBDKGGC (SEQ ribosomal proteins were generally meagerly expressed. Microarray hybridizations performed with MTP-based reverse transcription identified 1 to 12 more genes involved in each biological process than did microarrays performed using oligo-dT primers only (Table 3). MTPs outperformed oligo-dT primers most strikingly in their ability to reveal differentially expressed genes in the category of unknown and unclassified proteins (FIG. 1b). A gene involved in control of sexual development, encoding clock controlled pheromone ccg-4 precursor, was among genes differentially expressed in N. crassa protoperithecia.

Microarray Profiling of Pseudomonas syringae

Using protocols outlined above, an MTP was designed and tested for the prokaryotic organism Pseudomonas syringae pv phaseolicola. The MTP is 5'-DBMDBKBCDS SS-3' (SEQ ID NO:3) and is 23328-fold degenerate. This MTP provides an exact-match primer for 90.4% of 4985 mRNA sequences.

Using Nimblegen commercial microarrays and standard hybridization protocols, we found a high overlap between genes revealed as statistically significantly differentially expressed by MTP primers and N6 only. 261 genes overlapped in these two experiments. The N6 alone detected a total of 356 statistically significantly differentially expressed genes, while the MTP primer revealed a remarkably higher number of genes as statistically significantly differentially expressed (464). This represents an improvement of sensitivity of over 30%.

What is claimed is:

1. A method of generating a library of expressed cDNA sequences, comprising the steps of:
   (1) providing one or more RNA sequences from a genome database of a selected organism;
   (2) identifying one or more degenerate motifs that bind to a large proportion of mRNA sequences, said one or more identified degenerate motifs being located at multiple sites within said one or more mRNA sequences, in the steps of:
   randomly defining a degenerate oligonucleotide sequence;
   for the degenerate oligonucleotide sequence, calculating a score according to the formula:

$$\text{Score} = \frac{mRNAhits}{\#\ mRNAs * (1 + tRNAhits + rRNAhits)}$$

where mRNA hits, tRNA hits, and rRNA hits are the number of hits of said degenerate oligonucleotide sequence to the annotated mRNAs, tRNAs, and rRNAs, respectively, and #mRNAs is the total number of annotated mRNAs;

---

SEQUENCE LISTING

<160> NUMBER OF SEQ ID NOS: 3

<210> SEQ ID NO 1
<211> LENGTH: 12
<212> TYPE: DNA
<213> ORGANISM: Artificial Sequence
<220> FEATURE:
<223> OTHER INFORMATION: Engineered Multi-Targeted Primer Sequence
<220> FEATURE:
<221> NAME/KEY: misc_feature
<222> LOCATION: 1
<223> OTHER INFORMATION: n = any nucleotide

<400> SEQUENCE: 1
ndktbbbbdw gs                                                    12

<210> SEQ ID NO 2
<211> LENGTH: 12
<212> TYPE: DNA
<213> ORGANISM: Artificial Sequence
<220> FEATURE:
<223> OTHER INFORMATION: Engineered Multi-Targeted Primer Sequence
<220> FEATURE:
<221> NAME/KEY: misc_feature
<222> LOCATION: 3, 5, 6
<223> OTHER INFORMATION: n = any nucleotide

<400> SEQUENCE: 2
vwnvnnbdkg gc                                                    12

<210> SEQ ID NO 3
<211> LENGTH: 12
<212> TYPE: DNA
<213> ORGANISM: Artificial Sequence
<220> FEATURE:
<223> OTHER INFORMATION: Engineered Multi-Targeted Primer Sequence

<400> SEQUENCE: 3
dbmdbkbcds ss                                                    12 randomly mutating the degenerate oligonucleotide sequence;

calculating the score for the randomly mutated degenerate oligonucleotide sequence;

comparing the score for the randomly defined degenerate oligonucleotide sequence with the score for the randomly mutated degenerate oligonucleotide sequence;

(3) based on the comparison, providing one or more multi-targeted primers that are complementary to one or more of said degenerate motifs; and (4) combining said multi-targeted primers with mRNA molecules obtained from the organism in a reverse transcription assay to generate a library of expressed cDNA sequences.

2. The method of claim 1, wherein said organism is eukaryotic.

3. The method of claim 2, wherein said organism is *Neurospora crassa* or *Saccharomyces cerevisiae*.

4. The method of claim 1, wherein said organism is prokaryotic.

5. The method of claim 4, wherein said organism is *Pseudomonas syringae*.

6. The method of claim 1, wherein the steps of:

randomly mutating the degenerate oligonucleotide sequence;

calculating the score for the randomly mutated degenerate oligonucleotide sequence; and comparing the score for the randomly defined degenerate oligonucleotide sequence with the score for the randomly mutated degenerate oligonucleotide sequence are iterated.

7. The method of claim 1, wherein said step of providing one or more multi-targeted primers further comprises providing an oligo-dT primer.

8. The method of claim 1, wherein the multi-targeted primer has the sequence of NDKTBBBBDWGS (SEQ ID NO:1) or VWNVNNBDKGGC (SEQ ID NO:2).

9. A method of reverse mRNA transcription, comprising the steps of:

(1) providing a multi-targeted primer, having the sequence of NDKTBBBBDWGS (SEQ ID NO:1) or VWNVNNBDKGGC (SEQ ID NO:2);

(2) providing an oligo-dT primer;

(3) combining said multi-targeted primer and said oligo-dT primer with mRNA in a reverse transcription assay; and (4) reverse transcribing said mRNA.

10. The method of claim 9, wherein said mRNA is eukaryotic.

11. The method of claim 10, wherein said mRNA is from *Neurospora crassa* or *Saccharomyces cerevisiae*.

12. The method of claim 9, wherein said mRNA is prokaryotic.

13. The method of claim 12, wherein said mRNA is from *Pseudomonas syringae*.

14. The method of claim 1, wherein the one or more mRNA sequences lack poly-A tails.

15. The method of claim 9, wherein the multi-targeted primer is complementary to one or more degenerate motifs present in one or more mRNA sequences.

* * * * *